United States Patent [19]
Gilmer et al.

[11] Patent Number: 5,965,428
[45] Date of Patent: Oct. 12, 1999

[54] CHIMERIC LEPIDOPTERAN-TOXIC CRYSTAL PROTEINS

[75] Inventors: Amy Jelen Gilmer, Langhorne; James A. Baum, Doylestown, both of Pa.

[73] Assignee: Ecogen, Inc., Langhorne, Pa.

[21] Appl. No.: 08/731,079

[22] Filed: Oct. 8, 1996

[51] Int. Cl.[6] .................................. C12N 1/20; C07K 1/00
[52] U.S. Cl. .............................. 435/252.3; 435/252.31; 435/252.5; 530/350
[58] Field of Search ........................... 530/324, 333, 530/350, 820, 825; 435/69.1, 410, 419, 243, 252.3, 252.31, 320.1, 832, 252.5; 514/2, 33.1

[56] References Cited

U.S. PATENT DOCUMENTS

| | | | |
|---|---|---|---|
| 4,990,332 | 2/1991 | Payne et al. | 424/93 |
| 4,996,156 | 2/1991 | Zaehner et al. | 435/252.5 |
| 5,006,336 | 4/1991 | Payne et al. | 424/93 |
| 5,055,294 | 10/1991 | Gilroy | 424/93 |
| 5,188,960 | 2/1993 | Payne et al. | 435/252.3 |
| 5,322,687 | 6/1994 | Donovan et al. | 424/93 |
| 5,441,884 | 8/1995 | Baum | 435/252.31 |
| 5,508,264 | 4/1996 | Bradfisch et al. | 514/12 |
| 5,527,883 | 6/1996 | Thompson et al. | 530/350 |
| 5,593,881 | 1/1997 | Thompson et al. | 435/240.1 |
| 5,616,319 | 4/1997 | Donovan et al. | 424/93.2 |
| 5,650,308 | 7/1997 | Baum | 435/172.3 |
| 5,679,343 | 10/1997 | Donovan et al. | 424/93.461 |
| 5,686,069 | 11/1997 | Payne et al. | 424/93.461 |

FOREIGN PATENT DOCUMENTS

| | | |
|---|---|---|
| 0 099 301 | 7/1983 | European Pat. Off. . |
| 0 228 228 | 12/1986 | European Pat. Off. . |
| WO 91/07481 | 11/1990 | WIPO . |
| WO 91/16434 | 4/1991 | WIPO . |
| WO 95/02058 | 7/1994 | WIPO . |
| WO 95/30752 | 5/1995 | WIPO . |
| WO 95/30753 | 5/1995 | WIPO . |

*Primary Examiner*—Eggerton A. Campbell
*Assistant Examiner*—Devesh Srivastava
*Attorney, Agent, or Firm*—Woodcock Washburn Kurtz Mackiewicz & Norris, LLP

[57] ABSTRACT

The present invention is directed to a chimeric crystal protein comprising CryIF and CryIAc. *Bacillus thuringiensis* isolates comprising said protein and a method of controlling lepidopterans are also included in the present invention.

4 Claims, 7 Drawing Sheets cryIF protoxin

NH₂ ▼ ▼▼▼▼▼▼ COOH cryIF-IAc protoxin

NH₂ ▼ ▼▼▼▼▼ COOH proteolysis in the insect midgut active toxin active toxin

| CryIF core toxin domain | ■ |
| --- | --- |
| CryIF tail domain | □ |
| CryIAc tail domain | ▨ |

↓
binding to midgut "receptor" proteins
↓
intercalation into the brush border membrane
↓
formation of ion channels and pores
↓
osmotic imbalance, lysis of midgut epithelial cells
↓
insect mortality

Figure 1

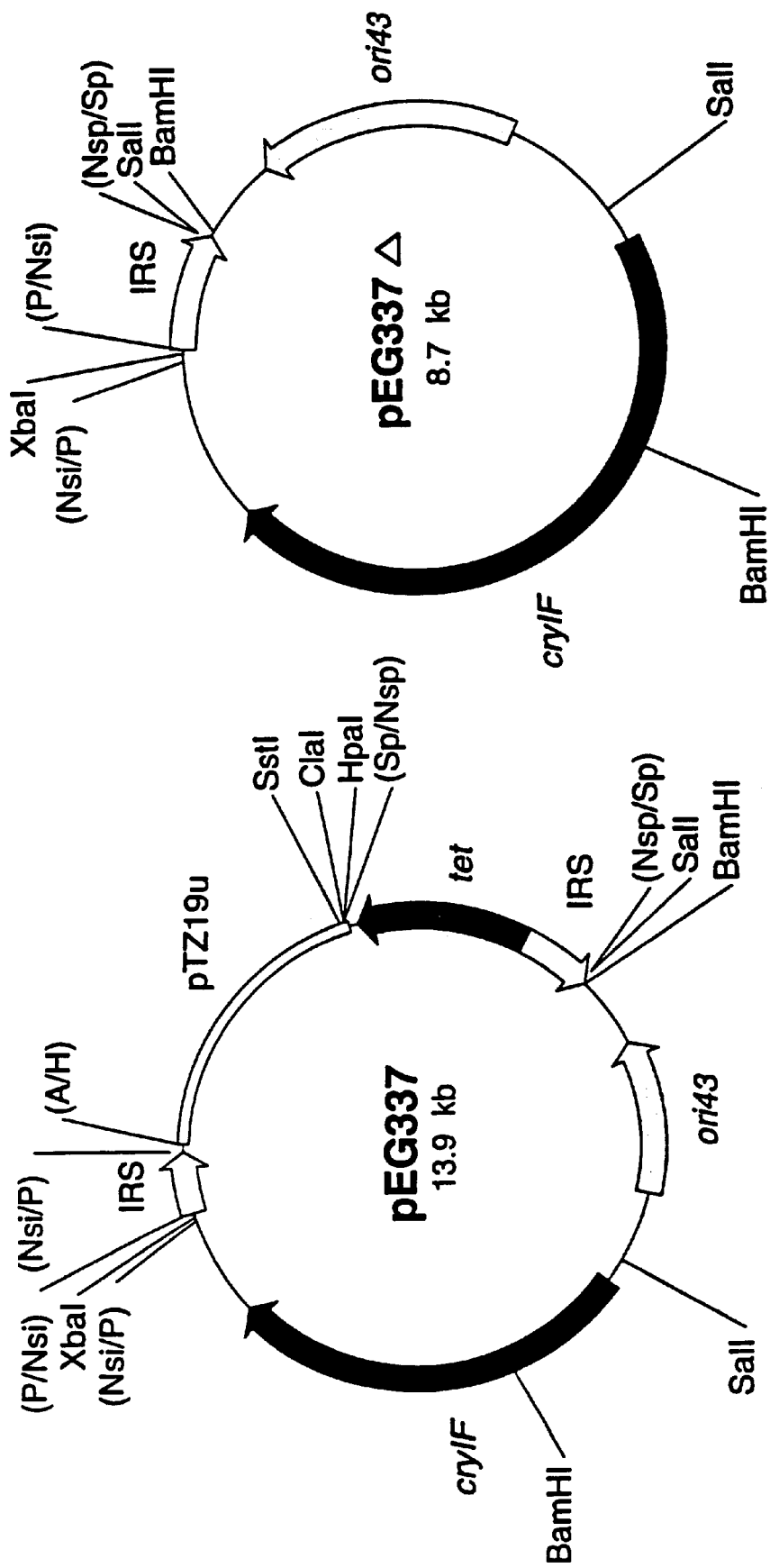

CHIMERIC LEPIDOPTERAN-TOXIC CRYSTAL PROTEINS

FIELD OF THE INVENTION

The present invention relates to chimeric lepidopteran-toxic crystal proteins that contribute to increased crystal protein production when introduced into a *Bacillus thuringiensis* strain harboring other lepidopteran-toxic crystal proteins. The invention also relates to recombinant *Bacillus thuringiensis* strains harboring the chimeric crystal protein gene that produce increased amounts of lepidopteran-toxic crystal protein.

BACKGROUND OF THE INVENTION

*Bacillus thuringiensis* ("*B.t.*") is a gram-positive bacterium that typically produces proteinaceous crystalline inclusions during sporulation. These *B.t.* crystal proteins are highly toxic to certain insects. Crystal proteins from various *B.t.* strain isolates have been identified as having insecticidal activity against insect larvae from the insect orders Lepidoptera (caterpillars), Coleoptera (beetles), Diptera (mosquitoes, flies), and Homoptera (aphids). The insecticidal crystal proteins (ICPs) of *B. thuringiensis* were originally classified as CryI, CryII, CryIII, and CryIV proteins based on their insecticidal activities (Hofte H. and H. R. Whiteley, *Microbiol. Rev.* 53:242–255 (1989)). The Hofte and Whiteley (1989) review provides an overview of the *B.t.* insecticidal crystal protein genes. CryI proteins, which encompass crystal proteins of approximately 130–140 kilodaltons (kDa) in molecular mass, display lepidopteran toxicity. CryII proteins are approximately 71 kDa in mass and may display both lepidopteran and dipteran toxicity. CryIII proteins are approximately 73–74 kDa in mass and display coleopteran toxicity. The CryIV proteins represent a diverse group of proteins that exhibit dipteran toxicity. For the purpose of the present invention, the Hofte and Whiteley nomenclature will be used.

Commercial *B.t.* bioinsecticide products currently being marketed for lepidopteran insect control are based on either naturally occurring ("native") strains or transconjugants strains. Transconjugant strains are created by transferring a crystal protein-encoding plasmid from a donor strain to a recipient strain via a conjugation-like process, resulting in a new *B.t.* strain. Plasmids may also be transferred from one strain to another by phage transduction. Native and transconjugant strains are fermented in a broth medium, the spores and crystals harvested, either by spray-drying or by centrifugation, and subsequently formulated for spray application.

The insecticidal activity of conventional *B.t.* bioinsecticides results from insect larvae feeding on the crystal protein, typically in sprayed-on deposits of the bioinsecticide on leaves or other plant surfaces. General details of the mode of action of the insecticidal crystal proteins (ICPs) are apparent. The ICPs contained within the proteinaceous crystals are released into the insect midgut after ingestion and solubilization of the crystals. In many instances, the full-length proteins or protoxins are processed by midgut proteases to a fully active state. The 130–140 kDa CryI protoxins, for instance, are processed to a core toxin moiety of 60–65 kDa, derived from the amino terminal half of the full-length protoxin. This processed core toxin is regarded as the active toxin within the insect midgut. The discarded carboxyl domain of the protoxin, though not essential for toxicity, is apparently indispensable for CryI crystal formation in *B.t.* For purposes of the present invention, the carboxyl half of the CryI protein not contained within the active or core toxin will be referred to as the tail domain. As depicted in FIG. 1, the processed, activated toxin, derived from the chimeric CryIF-IAc crystal protein of the present invention, binds to the brush border membranes (BBMs) of the insect midgut epithelium, a step that frequently requires the presence of fortuitous "receptor" proteins. This binding is followed by an apparent intercalation event in which the active toxin moiety, or a portion of it, contributes to the formation of ion channels as well as aggregates to form larger pores within the BBM, leading to osmotic imbalance, cellular swelling and lysis. Intoxicated insect larvae stop feeding within minutes and eventually die.

For many lepidopteran insect pests, such as armyworms, the *B.t.* spore present in the bioinsecticide formulation also contributes substantially to toxicity. The synergistic effect of spores has been reported for a number of important lepidopteran insect pests, including *Spodoptera exigua* (Moar, W. J., et al., *Appl. Environ. Microbiol.* 61:2086–2092 (1995)), *Lymantria dispar* (DuBois, N. and D. H. Dean., *Biological Control* 24:1741–1747 (1995)), and *Plutella xylostella* (Tang, J. D., et al., *Appl. Environ. Microbiol.* 62:564–569 (1996)). This spore effect on the insecticidal activity of *B.t.* is apparently due to septicemia: the ability of the spore to germinate within the insect midgut, to penetrate the disrupted midgut epithelium, and to enter and proliferate within the hoemcoel. For many lepidopteran insect pests, it is therefore desirable that the *B.t.* bioinsecticide formulation contain a mixture of spores and crystals to achieve maximal efficacy.

Among the lepidopteran insect pests, armyworms are particularly difficult to control, regardless of the insecticide used. Thus, there is a need for bioinsecticide products for armyworm control that are both efficacious and cost-effective. To satisfy this need, the amount of crystal protein produced by *B.t.* in fermentation should be maximized as much as possible in order to provide for its economic and efficient utilization in the field. Increased concentration of crystal protein in the formulated bioinsecticide promotes use of reduced amounts of bioinsecticide per unit area of treated crop, without reducing the actual amount of crystal protein applied per unit area, thereby allowing for more cost-effective use of the bioinsecticide product. Alternatively, increased fermentation yields of crystal protein, resulting in more concentrated formulations, may be used to increase the amount of crystal protein applied per unit area, thereby enhancing the performance of the bioinsecticide product.

Previous efforts to create mutants or variants of *B.t.* strains that show enhanced production of crystal proteins have related primarily to the production of coleopteran- or dipteran- toxic crystal proteins, not CryI lepidopteran-toxic crystal proteins. Also, most of these examples describe oligosporogenous or asporogenous (produce few, if any, spores) variants of *B.t.* that show increased crystal protein production. As noted above, the full production of spores is a desirable feature for a lepidopteran-active *B.t.* strain used for the production of a comnmercial bioinsecticide.

U.S. Pat. No. 5,006,336, issued to Payne, describes a native *B.t.* isolate (PS122D3), active against coleopteran insects, which produces more coleopteran-toxic protein (CryIIIA) than does an unrelated coleopteran-toxic *B.t.* strain, *B.t. san diego*. Strain PS122D3 is not a variant of *B.t.* strain *san diego*.

U.S. Pat. No. 4,996,156, issued to Zaehner et al., describes a dipteran-active *B.t. israelensis* mutant strain which produces crystal proteins but is asporogenous.

Published European Patent Application Publication No. O 099 30 of Fitz-James, describes mutants of *B.t. israelensis*, obtained using a chemical mutagen, that produces up to 1.5 times the amount of dipteran-toxic crystal protein as does the progenitor strain.

Published European Patent Application Publication No. O 228 228, of Mycogen Corporation, describes asporogenous *Bacillus thuringiensis* mutants obtained by treatment of the progenitor strains with ethidium bromide. Such *B.t.* mutants are described as being more efficient at producing coleopteran-toxic (CryIIIA) crystal protein.

Published PCT International Patent Application Publication No. WO 91/07481, of Novo Nordisk A/S, describes a mutant of *Bacillus thuringiensis tenebrionis*, which was obtained by gamma irradiation and which produces two times the amount of coleopteran-toxic crystal protein (CryIIIA) obtained from the progenitor strain.

U.S. Pat. No. 4,990,332, issued to Payne et al., describes a lepidopteran-toxic *B.t. kurstaki* mutant strain (PS85al-168) that produces crystal protein in amounts "equal to or higher than the wild type" but is asporogenous.

The efficacy and cost effectiveness of a *B. thuringiensis*-based bioinsecticide product may also be improved by manipulation of the crystal protein composition in the bioinsecticide product, engineering of crystal proteins for improved insecticidal activity or stability, and by improvements in the formulation that promote longer shelf-life and longer persistence upon field application.

With respect to engineered crystal proteins, Geiser and Moser, in published Canadian Patent Application No. 2035199, disclose a chirneric CryIAb-CryIAc protoxin that shows improved temperature stability when compared to the native CryIAb protoxin. The native CryIAb protoxin does not form crystal protein inclusions in *B. thuringiensis* when grown at temperatures of 30–35° C., the preferred temperature for cultivation of *B. thuringiensis*, and therefore cannot be produced efficiently in *B. thuringiensis* under these conditions. The chimeric CryIAb-CryIAc-protein, in which most of the carboxyl half or tail domain of the CryIAb protein has been replaced with that of the CryIAc protein, forms crystal protein inclusions in *B. thuringiensis* at 30° C. and thus can be produced efficiently. This chimeric protoxin was reported to have the same toxicity profile for *H. virescens* and *Trichoplusia* ni larvae as the parental CryIA(b) protoxin (Aronson, A. 1993. Insecticidal toxins in *Bacillus subtilis* and other gram-positive bacteria. Sonensheim, A. L., Hoch, J. A., and Losick, R. (eds.). Am. Soc. Microbiol., Washington D. C., pp. 953–963). Furthermore, the reciprocal chimeric protein, in which most of the carboxyl half or tail domain of the CryIAc protein has been replaced with that of CryIAb, does not form stable inclusions in *B.t.* at the preferred cultivation temperature thus mimicing the temperature sensitive crystal forming phenotype of CryIAb.

Thompson et al., in PCT International Publication No. WO 95/30752, disclose a chimeric CryIC-CryIAb protoxin that shows improved insecticidal activity when produced in *Pseudomonas fluorescens*. This protoxin alone may not be produced efficiently in *B. thutingiensis* at the preferred cultivation temperature because it contains the tail domain of CryIAb that confers the temperature-sensitive crystal-forming phenotype of CryIAb described by Geiser and Moser.

A cryIF lepidopteran-toxic crystal protein gene is described in U.S. Pat. No. 5,188,960 issued to Payne et al., and in PCT International Publication No. WO 91/16434 of Ecogen Inc. Chambers et al. (1991) J. Bacteriol. 173:3966–3976, discloses a cryIF crystal protein gene from *B.t.* strain EG6346 subsp. *aizawai* and the insecticidal activity of its encoded CryIF crystal protein. A recombinant *B.t.* strain expressing this cryIF gene and designated strain EG7826 is disclosed by Baum in PCT International Publication No. WO 95/02058. Thompson and Schwab, in PCT International Publication No. WO 95/30753, disclose a chimeric CryIF-CryIAb protoxin that can be produced more efficiently in *Pseudomonas fluorescens* than the native CryIF protoxin. By analogy to the work of Geiser and Moser, the production of this chimeric CryIF-CryIAb protoxin in *B. thuringiensis*, at the preferred cultivation temperature, would be expected to be less efficient than that of the native CryIF protein. Thus, the requirements for efficient expression in *B. thuringiensis* and Pseudomonas appear to differ.

U.S. Pat. No. 5,508,264, issued to Bradfisch et al.discloses a synergistic effect as a result of the combination of the chimeric CryIF crystal protein and a chimeric CryIAc crystal protein produced in *Pseudomonas fluorescens*. The disclosed chimeric CryIF proteins includes the chimeric CryIF-CryIAb protoxin or a chimeric CryIF-CryIAc/CryIAb protoxin. The protoxin domain of the latter protein is comprised of both CryIAb and CryIAc sequences.

There is a need to improve the efficacy and cost-effectiveness of lepidopteran-toxic insecticides, particularly those used for the control of armyworms. This may be achieved, in part, by improving the amount of CryI crystal protein obtained in fermentation, thereby allowing for more economic use of the crystal protein in bioinsecticide formulations. The toxicity of the bioinsecticide product towards armyworms may be further improved by the use of a *Bacillus thuringiensis* strain that is proficient in the production of spores as well as in the production of CryI crystal protein. As evidenced by the prior art, standard methods for optimizing the production of CryI crystal proteins in a spore-forming entomopathogenic bacterium such as *Bacillus thuringiensis* remain elusive.

SUMMARY OF THE INVENTION

The chimeric CryIF-CryIAc protein of the present invention is comprised of amino acids from about 1 to about 718 of a native CryIF protein which includes a core toxin region of a CryIF protein. The remaining carboxyl terminal portion of the chimeric protein is comprised of amino acids from about 727 to about 1178 of a CryIAc protein. The *Bacillus thuringiensis* (*B.t.*) strain of this invention includes a biologically pure culture of a *Bacillus thufingiensis* bacterium deposited with the Agricultural Research Service Culture Collection, Northern Regional Research Laboratory (NRRL), having accession number NRRL B-21508 and being designated as EG11724. *B.t.* strain EG11724 sporulates efficiently and produces more CryI lepidopteran-toxic crystal protein than does the CryIF-producing strain EG7826.

The present invention also embodies insecticide compositions comprising the *B.t.* strains of the present invention, insecticidal proteins produced by such B.t. strains together with an agriculturally acceptable carrier, and to the methods of using such insecticidal compositions for insect control.

BRIEF DESCRIPTION OF THE DRAWINGS

FIG. 1 depicts a schematic diagram showing steps in the mode of action of CryI insecticidal crystal proteins.

FIG. 2B comprises a structural map of the recombinant plasmid pEG317, containing the crtyIF insecticidal crystal protein gene from B. thuringiensis strain EG6346. Boxes and arrows indicate genes or functional DNA elements. Designations: pTZ19u =E. coli phagemid vector pTZ19u, cat=chloramphenicol acetyl transferase gene, ori44=B. thuringiensis plasmid replication origin, cryIF=insecticidal crystal protein gene, cryV=cryptic insecticidal crystal protein gene. FIG. 2C comprises a structural map of the recombinant plasmid pEG861, containing a cryIAc insecticidal crystal protein gene. Boxes and arrows indicate genes or functional DNA elements. Designations: pTZ19u=E. coli phagemid vector pTZ 19u, cat=chloramphenicol acetyl transferase gene, ori43=B. thuringiensis plasmid replication origin, cryIAc= insecticidal crystal protein gene.

FIG. 5 comprises a structural map of the recombinant plasmid pEG337, containing the cryIF insecticidal crystal protein gene, and the derivative of pEG337, designated pEG337Δ, present in strain EG7826. The boxes and arrows indicate genes or functional DNA elements. Designations: pTZ19u=E. coli phagemid vector pTZ 19u, tet=tetracycline resistance gene, ori43=B. thuringiensis plasmid replication origin, cryIF=insecticidal crystal protein gene, IRS=DNA fragments containing the internal resolution site region of transposon Tn5401. Restriction endonuclease site abbreviations: A=Asp718, H=HindIII, Nsi=NsI, Nsp=NspI, P=PstI, Sal=SalI, Sp=SphI, Xho=XhoI.

DETAILED DESCRIPTION OF THE INVENTION

Figure 2A:
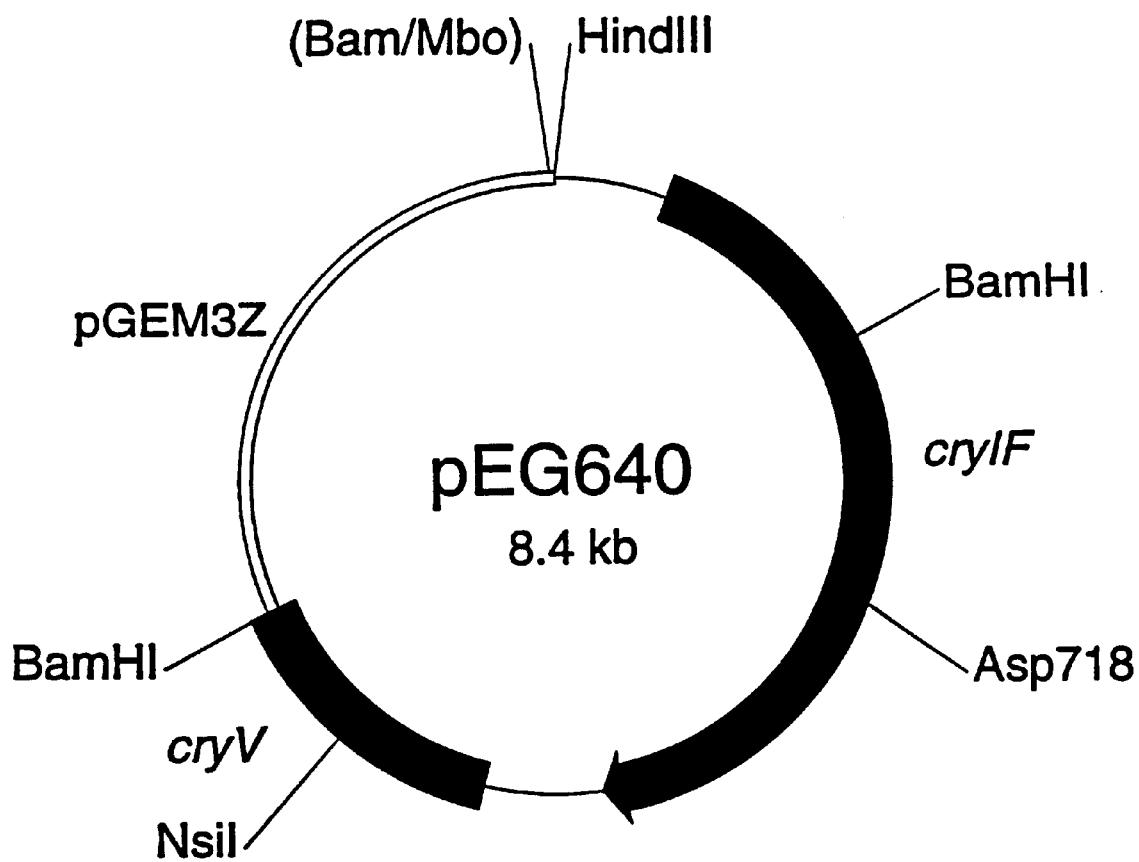
FIGS. 2A–2C comprises a structural map of the recombinant plasmid pEG640, containing the cryIF insecticidal crystal protein gene from B. thuringiensis strain EG6346 subsp. aizawai. The solid boxed arrow indicates the cryIF gene, the solid box indicates the 5' portion of a cryptic cryV gene, and the narrow open box indicates the DNA fragment containing pGEM3Z, an E. coli cloning vector. Restriction site abbreviations: Bam=BamHI, Mbo=MboI.

The present invention is directed to a chimeric protein comprising a CryIF core toxin-containing portion and a CryIAc tail-containing portion. Crystal proteins may be characterized as comprising an amino terminus and a carboxyl terminus. The core toxin portion is in the amino terminus of the crystal protein and the tail is in the carboxyl terminus of the crystal protein. CryI crystal proteins comprise about 1150 to about 1200 amino acids. In CryIF, amino acids of about 1to about 718 (SEQ ID NO: 1) comprise the core toxin portion and in CryIAc, amino acids of about 727 to about 1178 (SEQ ID NO: 2) comprise the tail portion of the about 1150 to about 1200 total amino acids in the protein. In the chimeric protein of the present invention, the amino acid sequence encoded by the cryIAc codons 727–745 is identical to the amino acid sequence encoded by the cryIF codons 719–737. Thus, the sequence of the chimeric protein of the present invention from amino acids 1–737 is identical to that of CryIF. A chimeric protein for purposes of the present invention, is a protein that derives the core toxin from one crystal protein while the tail is derived from a crystal protein different from the crystal protein providing the core toxin, such that the portions are heterologous. The chimeric crystal protein of the present invention is preferably isolated and purified. A preferred embodiment of the present invention provides a core toxin-containing portion from CryIF and a tail-containing portion from CryIAc. The chimeric protein of the present invention is about 1150 to about 1200 amino acids, more preferably about 1170 amino acids in length. The CryIF core toxin-containing portion of the chimeric protein of the present invention substantially comprises CryIF core toxin sequence. The CryIAc tail-containing portion of the chimeric protein of the present invention substantially comprises CryIAc tail sequence. For purposes of the present invention, substantially refers to about 50%, more preferably about 75%, even more preferably about 90%, and most preferably about 100% of the core toxin sequence for CryIF and tail sequence for CryIAc. For purposes of the present invention, amino acid sequences include peptide, protein, protoxin, and toxin sequences within the scope of the present invention include, and are not limited to all or part of the sequences set forth in SEQ ID NOS: 1 and 2, sequences substantially similar thereto, and alterations in the amino acid sequences including alterations, deletions, mutations, and homologs, and synthetic sequences. For purposes of the present invention, the phrase "substantially similar" refers to sequences having amino acids at certain aligned positions in common at least about 50%, preferably about 75%, more preferably at least about 90%, and most preferably, about 100%. In addition, substantially similar sequences have substantially similar CryIF-CryIAc activity exhibited by the CryIF-CryIAc chimeric protein of the present invention.

The present invention relates to a chimeric cryIF-cryIAc crystal protein gene, designated cryIF-IAc or cryIF-cryIAc, that contributes to enhanced crystal protein production compared to cryIF when expressed in a *Bacillus thuringiensis* host strain containing other cryI genes. The insecticidal activity of the chimeric protein, designated CryIF-IAc or CryIF-CryIAc, is similar to that of the native CryIF protein. A recombinant strain containing the chimeric gene, designated EG11724, produces 30–40% more CryI crystal protein than does an isogenic strain containing the native cryIF gene, designated EG7826. The two recombinant *B.t.* strains are indistinguishable with respect to their sporulation efficiency and insecticidal activity against *Spodoptera frugiperda*. The increased production of lepidopteran-toxic protein obtained with the chimeric CryIF-IAc protein in strain EG11724 may be used to develop more concentrated or more cost-effective bioinsecticide formulations for the control of certain lepidopteran insect pests, particularly the fall armyworm *S. frugiperda*. For purposes of the present invention, lepidopteran-toxic is defined as toxic to at least one lepidopteran.

Nucleic acid sequences include and are not limited to DNA, including and not limited to cDNA and genomic DNA, genes; RNA, including and not limited to mRNA and tRNA; nucleosides, and suitable nucleic acid sequences such as all or part of those encoding the amino acid sequences of SEQ ID NOS:1 and 2, sequences substantially similar thereto, and alterations in the nucleic acid sequences including alterations, deletions, mutations, and homologs, and synthetic sequences capable of expressing cryIF-cryIAc of the present invention, as well as antisense sequences to all or part of the nucleic acid sequences.

The CryIF and CryIAc portions of the chimeric protein may be derived from any microorganism having crystal proteins, preferably, CryIF and CryIAc are derived from *Bacillus thuringiensis*. For purposes of the present invention, a microorganism includes and is not limited to an isolate comprising the chimeric CryIF-CryIAc protein or activity, derivatives of the isolate, and spores of the isolate.

The nucleotide sequences of the subject invention can be introduced into a wide variety of microbial hosts. Expression of the chimeric toxin gene results, directly or indirectly, in the intracellular production and maintenance of the insecticide. With suitable hosts, e.g., Bacillus, the microbes can be applied to the sites of lepidopteran insects where they will proliferate and be ingested by the insects. The results is a control of the unwanted insects. Alternatively, the microbe hosting the chimeric toxin gene can be treated under conditions that prolong the activity of the toxin produced in the cell. The treated cell then can be applied to the environment of target pest(s). The resulting product retains the toxicity of the *B. thuringiensis* toxin.

Suitable host cells, where the pesticide-containing cells will be treated to prolong the activity of the chimeric toxin in the cell when the then treated cell is applied to the environment of target pest(s), may include either prokaryotes or eukaryotes, typically being limited to those cells which do not produce substances toxic to higher organisms, such as mammals. However, organisms which produce substances toxic to higher organisms could be used, where the chimeric toxin is unstable or the level of application sufficiently low as to avoid any possibility or toxicity to a mammalian host. As hosts, of particular interest will be the prokaryotes and the lower eukaryotes, such as fungi. Illustrative prokaryotes, both Gram-negative and Gram-positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desutfovibrio, Spirillum; Lactobacillaceae; Pseudomonadaceae, such as Pseudomonas and Acetobacter, Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B. thuringiensis* sequences into the host, availability of expression systems, efficiency of expressions, stability of the pesticide in the host, and the presence of auxiliary genetic capabilities. Characteristics of interest for use as an insecticide microcapsule include protective qualities for the insecticide, such as thick cell walls, pigmentation, and intracellular packaging or formation of inclusion bodies; leaf affinity; lack of mammalian toxicity; attractiveness to insects for ingestion; ease of killing and fixing without damage to the chimeric toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Bacillus thuringiensis, Escherichia coli, Bacillus subtilis, Bacillus cereus, Bacillus megaterium, Pseudomonas aeruginosa, Pseudomonas fluorescens, Saccharomyces cerevisiae, Streptomyces lividans* and the like.

Treatment of the microbial cell, e.g., a microbe containing the *B. thuringiensis* chimeric toxin sequences, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol's iodine, Bouin's fixative, and Helly's fixatives, (see e.g., Humason, 1967); or a combination of physical (heat) and chemical agents that preserve and prolong the activity of the toxin produced in the cell when the cell is administered to the host animal. Examples of physical means are short wavelength radiation such as y-radiation and X-radiation, freezing, UV irradiation, lyophilization, and the like. The cells employed will usually be intact and be substantially in the proliferative form when treated, rather than in a spore form, although in some instances spores may be employed.

Where the *B. thuringiensis* chimeric toxin sequences are introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms for incorporating the *B. thuringiensis* chimeric toxin sequences, such as bacteria, e.g., genera Bacillus, Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomzyces, Cryptococcus, Kluyveromyces, Sporobolonyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodobacter sphaeroides, Xanthomonas campestris, Rhizobium melioti, Alcaligenes eutrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*.

A preferred novel *B. thuringiensis* isolate of the subject invention is designated EGI 1724. This isolate produces a chimeric lepidopteran-toxic crystal protein comprising CryIF core toxin-containing portion and a CryIAc tail-containing portion. Derivatives of the *B. thuringiensis* isolate EG11724 containing at least one of the chimeric crystal protein nucleotide sequences, are included within the present invention. This isolate and derivatives are capable of increased production of CryI crystal proteins.

The chimeric protein and the cells comprising the chimeric protein of the present invention are active against lepidopterans including and not limited to *Spodoptera exigua, Spodoptera frugiperda, Trichoplusia ni*, and *Plutella xylostella*.

*B. thuringiensis* may be cultured using standard known media and fermentation techniques. Upon completion of the fermentation cycle, the bacteria can be harvested by separating the *B.t.* spores and crystals from the fermentation broth by means well known in the art, such as and not limited to centrifugation. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. The *B.t.* isolates of the present invention can be used to control lepidopteran pests.

A subculture of *B.t.* was prepared in accordance with the methods set forth in the Examples and were deposited in the permanent collection of the Agricultural Research Service Culture Collection, Peoria, Ill.

The accession numbers are as follows:

| Strain Deposits | | |
| --- | --- | --- |
| Bacterial strain | NRRL Accession Number | Date of Deposit |
| EG7826 | NRRL B-21249 | May 10, 1994 |
| EG11724 | NRRL B-21508 | November 15, 1995 |
| EG1943 | NRRL B-18634 | March 27, 1990 |

The subject cultures have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to funish a sample when requested, due to the condition of the deposit(s). All restrictions on the availability to the public of the subject culture deposits will be irrevocably removed upon the granting of a patent disclosing them.

The *Bacillus thuringiensis* isolate EG11724 and derivatives thereof may be prepared by recombinant methods including and not limited to recombinant plasmids containing an insecticidal crystal protein gene and by phage transduction or by a conjugation-like process. A wide variety of ways are available for introducing a *B.t.* sequence expressing a core toxin and/or a protoxin into the *B. thuringiensis* host under conditions which allow for stable maintenance and expression of the sequences. One can provide for DNA constructs which include the transcriptional and translational regulatory signals for expression of the core toxin sequence, the core toxin sequence under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the core toxin, where expression of the core toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a core toxin, but upon release into the environment, expression would begin. Other techniques may employ a specific nutrient medium in the laboratory, which inhibits the expression of the core toxin, where the nutrient medium in the environment would allow for expression of the core toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the protein expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Where no functional replication system is present, the construct will also include a sequence of at least 50 basepairs (bp), preferably at least about 100 bp, more preferably at least about 1000 bp, and usually not more than about 2000 bp of a sequence homologous with a sequence in the host. In this way, the probability of legitimate recombination is enhanced, so that the gene will be integrated into the host and stably maintained by the host.

A number of transcriptional regulatory regions are available from *Bacillus thuringiensis*. Various transcriptional regulatory regions include the regions associated with the α amylase gene, phospholipase C gene, exoproteinase gene, and the naturally-occurring promoters associated with crystal proteins, which are functional in the host. See for example, Chak et al., *Appl. Environ. Microbiol.*, 1994, 60:2304–2310, PCT WO94/25611 of Sandoz Ltd., and PCT WO92/14826 of Ciba Geigy. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. For expression in Bacillus species, a large number of plasmids are available, such as pEG147, pHT3101, pEG597, pEG853, pEG854, pHV33, and the like. See for review, Gawron-Burke, C., and Baum, J. A., *Genetic Engineering* 1991, 13:237–263.

The crystal protein sequences can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity. When desired, unwanted or ancillary DNA sequences may be selectively removed from the recombinant bacterium by employing a site specific recombination system as described in U.S. Pat. No. 5,441,884.

The *B.t.* cells containing *B.t.* crystal protein sequences may be grown in any convenient nutrient medium that allows for efficient sporulation, where the DNA construct provides a selective advantage, providing for a selective medium so that substantially all or all of the cells retain the *B.t.* crystal protein sequences. Following fermentation, the spores and crystals may then be harvested in accordance with conventional methods.

The *B.t.* spores and crystals may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The insecticidal concentration will vary widely depending upon the nature of the particular formulation, particularly whether it is a concentrate or to be used directly. The insecticide will be present in at least 1% by weight and may be 100% by weight. The dry formulations will have from about 1% to about 95% by weight of the pesticide while the liquid formulations will generally be from about 1% to about 75% by weight of the solids in the liquid phase. The formulations will be administered at about 1 gram (liquid or dry) to about 1 kg or more per hectare.

The formulations can be applied to the environment of the lepidopteran pest(s), e.g., plants, soil or water, by spraying, dusting, sprinkling, or the like. Applications will be set with regard to conditions specific to the pest and environment such as and not limited to crop, weather conditions, insect pressure and population. The proportional ratio of active ingredient to carrier will naturally depend on the chemical nature, solubility, and stability of the insecticidal composition, as well as the dosage contemplated.

The insecticidal compositions of the invention may be employed in the methods of the invention singly or in combination with other compounds, including and not limited to other pesticides, such as and not limited to insect pheremones. The method of the invention may also be used in conjunction with other treatments. The insecticidal composition of the present invention may be administered by any suitable route, including and not limited to topical sprays.

To prepare phage resistant variants of B.t., an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

In yet another aspect, the present invention provides methods for producing a transgenic plant which expresses a nucleic acid segment encoding the novel chimeric crystal protein of the present invention. The process of producing transgenic plants is well-known in the art. In general, the method comprises transforming a suitable host cell with one or more DNA segments which contain one or more promoters operatively linked to a coding region that encodes one or more of the novel B. thuringiensis chimeric CryIF-CryIAc crystal proteins. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Another aspect of the invention comprises a transgenic plant which express a gene or gene segment encoding one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more CryIF-CryIAc-encoding transgenes, either recombinantly engineered, synthetically modified, or mutated. In some instances, more than one transgene will be incorporated into the genome of the transformed host plant cell. Such is the case when more than one crystal protein-encoding DNA segment is incorporated into the genome of such a plant. In certain situations, it may be desirable to have one, two, three, four, or even more B. thuringiensis crystal protein genes (either native or recombinantly-engineered) incorporated and stably expressed in the transformed transgenic plant.

A preferred nucleic acid sequence that may be introduced includes, for example, a CryIF core toxin-containing portion together with a CryIAc tail containing portion. Highly preferred nucleic acid sequences are those obtained from B. thuringiensis, or any of those sequences which have been genetically engineered to decrease or increase the insecticidal activity of the crystal protein in such a transformed host cell.

Means for transforming a plant cell and the preparation of a transgenic cell line are well-known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified crystal protein, which will be expressed in the resultant recombinant cells, and/or which will impart an improved phenotype to the regenerated plant.

Such transgenic plants may be desirable for increasing the insecticidal resistance of a monocotyledonous or dicotyledonous plant, by incorporating into such a plant, a transgenic DNA segment encoding a chimeric CryIF-CryIAc crystal protein which is toxic to lepidopteran insects. Particularly preferred monocutiledenous plants include corn and turf grass. Preferred dicotyledonous plants include lettuce, crucifers, and tomatoes.

In a related aspect, the present invention also encompasses a seed produced by the transformed plant, a progeny from such seed, and a seed produced by the progeny of the original transgenic plant, produced in accordance with the above process. Such progeny and seeds will have a stable crystal protein transgene stably incorporated into its genome, and such progeny plants will inherit the traits afforded by the introduction of a stable transgene in Mendelian fashion. All such transgenic plants having incorporated into their genome transgenic DNA segments encoding one or more chimeric CryIF-CryIAc crystal proteins or polypeptides are aspects of this invention.

A bacterium, a yeast cell, or a plant cell or a plant transformed with an expression vector of the present invention is also contemplated. A transgenic bacterium, yeast cell, plant cell or plant derived from such a transformed or transgenic cell is also contemplated. Means for transforming bacteria and yeast cells are well known in the art. Typically, means of transformation are similar to those well known means used to transform other bacteria or yeast such as *E. coli* or *Saccharomyces cerevisiae*.

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al, 1992); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

In one embodiment it is advantageous to use the novel nucleic acid sequences disclosed herein for the production of transgenic plants with increase insecticidal resistance to lepidopterans. The methods of producing transgenic plants are well-known in the art, but as a means of illustration, one can increase the insecticidal resistance of a plant, such as a monocotyledonous plant, (e.g., corn), by transforming such a plant with a crystal protein-encoding DNA segment using the particle bombardment methods (Maddock et al., 1991). By way of example, an expression vector containing a core toxin-containing portion of a *B. thuringiensis* CryIF crystal protein, a tail-containing portion of a *B. thuringiensis* CryIAc crystal protein, and an appropriate selectable marker is transformed into a suspension of embryonic maize (corn) cells using a particle gun to deliver the DNA coated on microprojectiles. Transgenic plants are regenerated from transformed embryonic calli that express the disclosed insecticidal crystal proteins. Particle bombardment has been used to successfully transform wheat (Vasil et al., 1992).

Alternatively, DNA can also be introduced into plants by direct DNA transfer into pollen as described (Zhou et al., 1983; Hess, 1987; Luo et al., 1988). Expression of polypeptide coding genes can be obtained by injection of the DNA into reproductive organs of a plant as described (Pena et al., 1987). DNA can also be injected directly into the cells of immature embryos and the rehydration of desiccated embryos as described (Neuhaus et al., 1987; Benbrook et al., 1986).

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus produces a chimeric CryIF-CryIAc protein. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against lepidopteran insects, preferably in the field, under a range of environmental conditions. The inventors contemplate that the present invention will find particular utility in the creation of transgenic plants.

For purposes of the present invention, transgenic cell refers to any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant. A transgenic plant refers to a plant or progeny thereof derived from a transformed plant cell or protoplast, wherein the plant DNA contains an introduced exogenous DNA molecule not originally present in a native, non-transgenic plant of the same strain.

The present invention is further described in the following examples. These examples are not to be construed as limiting the scope of the appended claims.

EXAMPLES

Example 1

Construction of a Chimeric CryIF-CryIAc Crystal Protein Gene

Figure 2B:
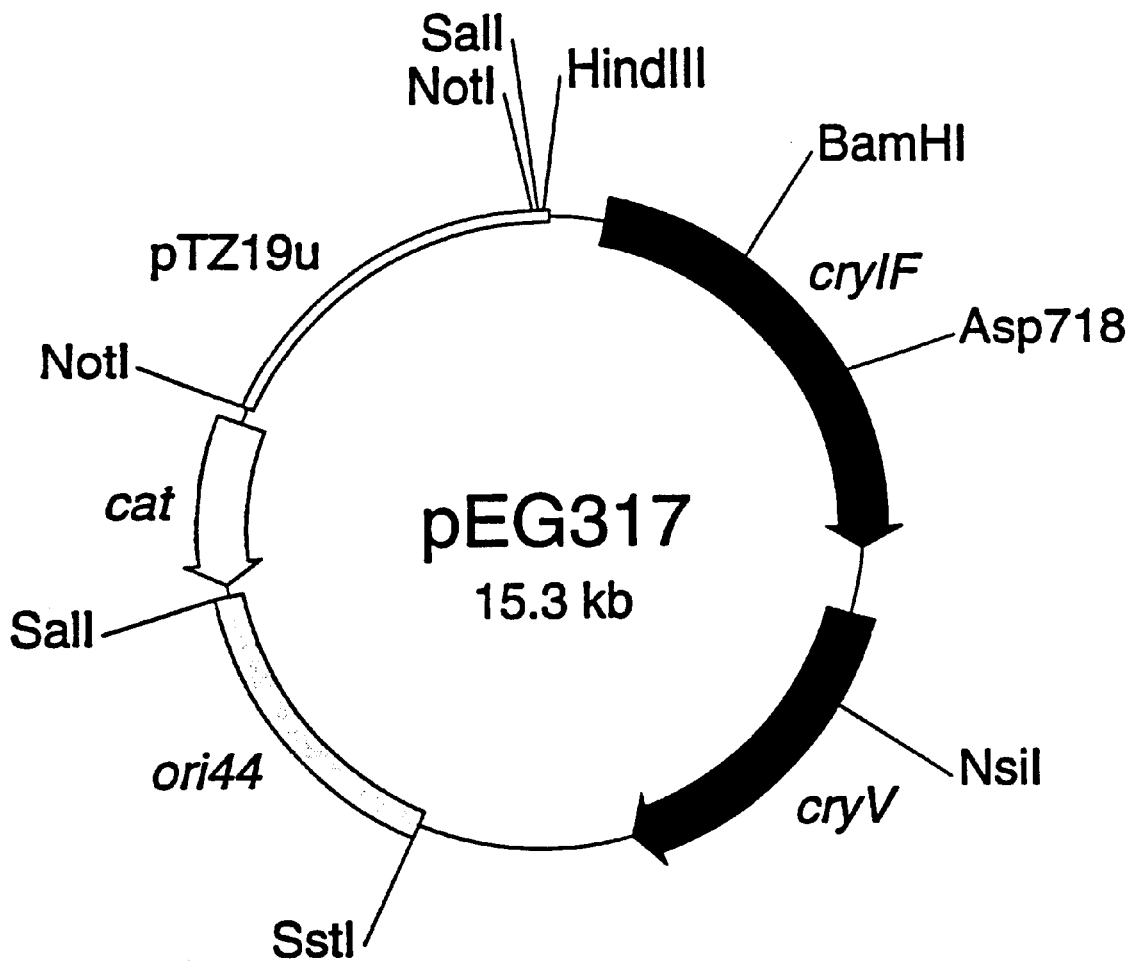
Figure 2C:
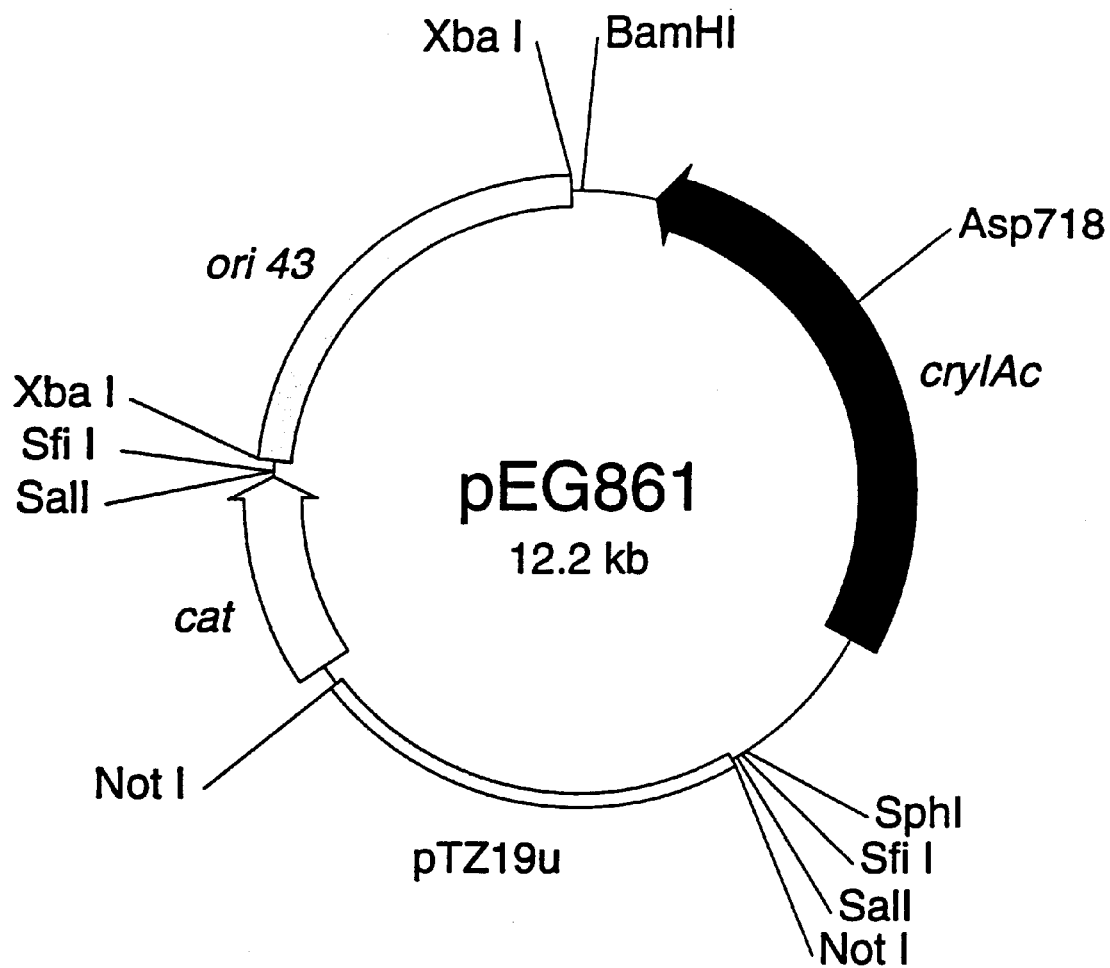

Schematic diagrams of two cryIF-containing plasmids are shown in FIG. 2. Plasmid pEG640, containing the native cryIF gene of B.t. strain EG6346 subsp. *aizawai*, was described by Chambers et al., *J. Bacteriol.* 173:3966–3976 (1991). This plasmid is propagated in the recombinant *E. coli* strain EG1943, described by Chambers et al. The cryIF gene fragment is also contained on a derivative of the *B.t.-E. coli* shuttle vector pEG597, described by Baum et al., *Appl. Environ. Microbiol.* 56:3420–3428 (1990), designated plasmid pEG317. Plasmid pEG317 contains an additional sequence 3' to the cryIF gene which contains a cryptic cryV gene.

Figure 3:
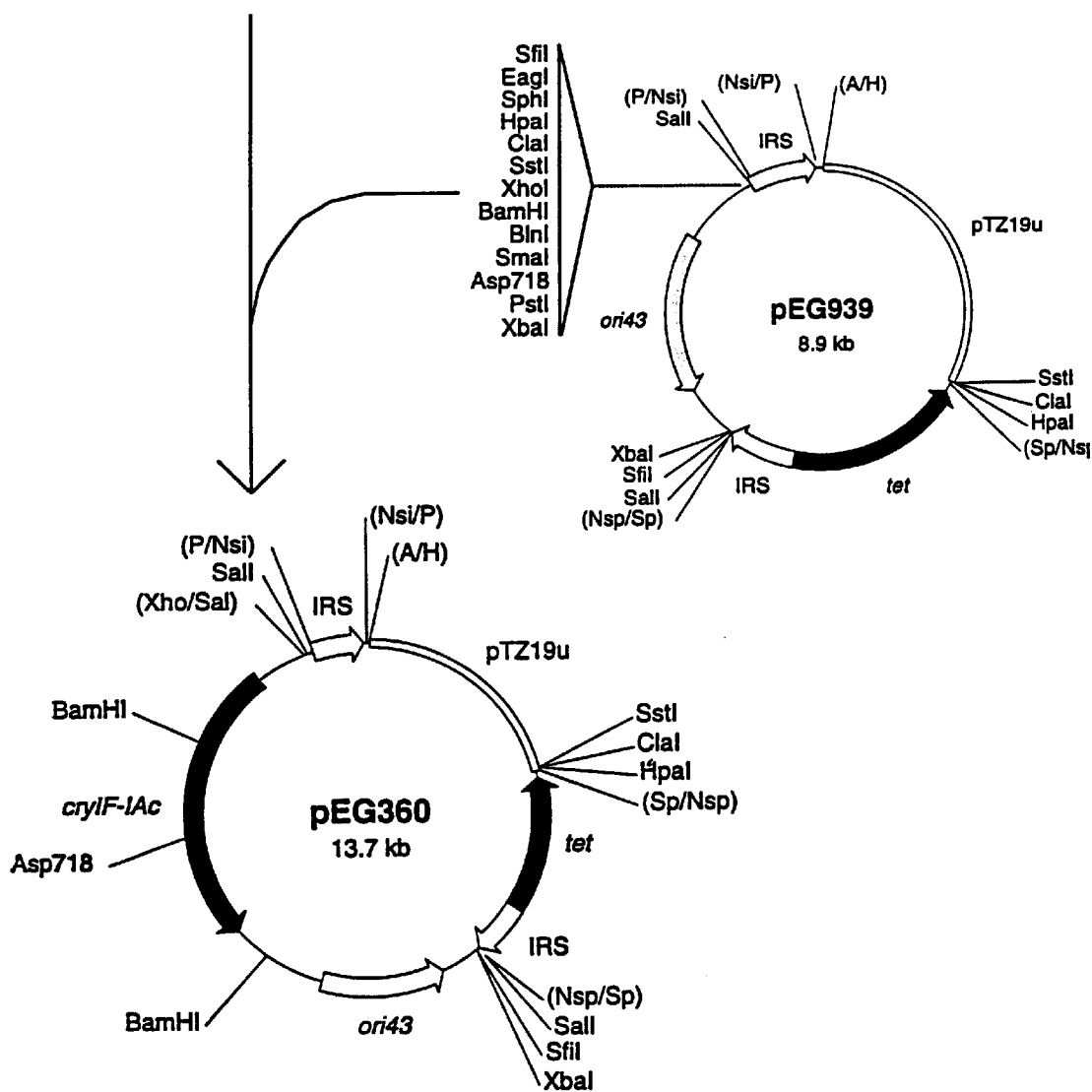
FIG. 3 comprises a schematic diagram showing the construction of the cryIF-IAc shuttle vector pEG360. Boxes and arrows indicate genes or functional DNA elements. Designations: pTZ19u=E. coli phagemid vector pTZ19u, tet= tetracycline resistance gene, ori43=B. thuringiensis plasmid replication origin, cryIF-IAc=insecticidal crystal protein gene, solid boxes=cryIF and cryIAcgene fragments obtained by restriction enzyme digestion, IRS=DNA fragments containing the internal resolution site region of transposon Tn5401. Restriction endonuclease site abbreviations: A=Asp718, H=HindIII, Nsi=NsiI, Nsp=NspI, P=PstI, Sal= SalI, Sp=SphI, Xho=XhoI.

The construction of the cryIF-cryIAc gene ("cryIF-IAc") of the present invention and the cryIF-IAc shuttle vector pEG360 is shown schematically in FIG. 3. The core toxin region of CryIF, contained on a ~2.8 kb SalI-Asp718 restriction fragment was isolated from the cryIF plasmid pEG317. This DNA fragment also contained the cryIF promoter region. A DNA fragment containing a 3' portion of the cryIAc gene was isolated as a ~2.0 kb Asp718-BamHI restriction fragment from the cryIAc shuttle vector pEG861 described by Baum et al., *Appl. Environ. Microbiol.* 56:3420–3428 (1990). This DNA fragment also contained the cryIAc transcription terminator region. In both cases, the DNA fragments were purified from ethidium bromide-stained agarose gels after electrophoresis using the Geneclean II kit (BIO 101, La Jolla, Calif.) following the manufacturers suggested protocol. The DNA fragments were ligated simultaneously into the unique XhoI and BamHI sites of the shuttle vector pEG939 (FIG. 3) using T4 ligase to generate plasmid pEG360. Shuttle vector pEG939 is similar in structure to shuttle vector p85, described in U.S. Pat. No. 5,441,884, but contains a multiple cloning site.

Ligation of the cryIF and cryIAc gene fragments via the Asp718-generated cohesive ends resulted in the formation of a chimeric cryI gene, designated cryIF-IAc. Ligation of the Asp718 cohesive ends regenerated codons 717 and 718 of cryIF, which are identical to codons 725 and 726 of cryIAc. The resulting gene thus comprised of codons 1–718 of cryIF followed by codons 727–1178 of cryIAc. Furthermore, since the amino acid sequence encoded by the cryIAc codons 727–745 is identical to the amino acid sequence encoded by the cryIF codons 719–737, the sequence of the chimeric protein from amino acids 1–737 is identical to that of CryIF.

Figure 4:
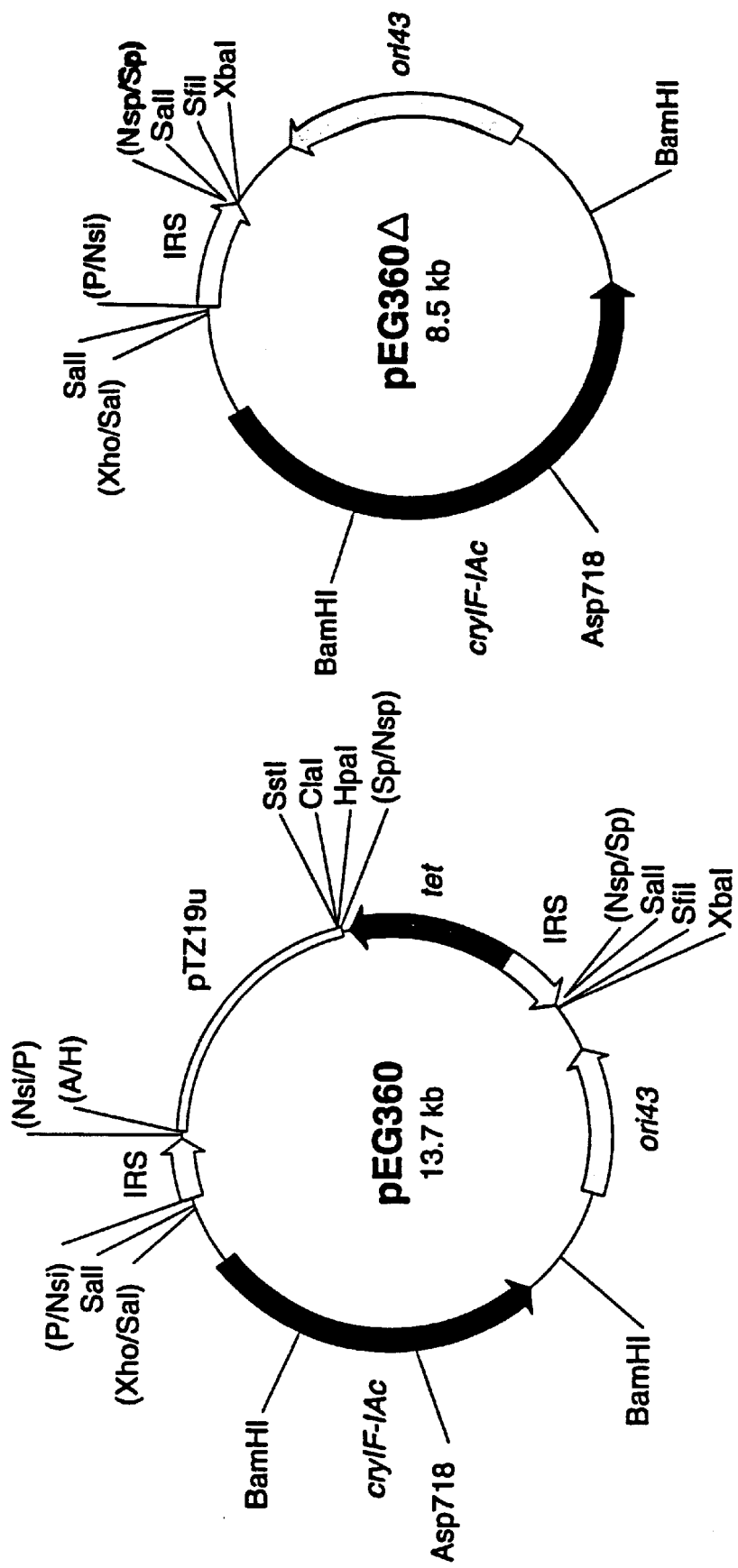
FIG. 4 comprises a structural map of the recombinant plasmid pEG360, containing the cryIF-IAc insecticidal crystal protein gene, and the derivative of pEG360, designated pEG360Δ, present in strain EG11724. The boxes and arrows indicate genes or functional DNA elements. Designations: pTZ19u=E. coli phagemid vector pTZ19u, tet=tetracycline resistance gene, ori43=B. thuringiensis plasmid replication origin, cryIF-IAc=insecticidal crystal protein gene, IRS= DNA fragments containing the internal resolution site region of transposon Tn5401. Restriction endonuclease site abbreviations: A=Asp718, H=HindIII, Nsi=NsiI, Nsp=NspI, P=PstI, Sal=SaI, Sp=SphI, Xho=XzoI.

The ligation mixture was used to transform the acrystalliferous B.t. host strain EG10368, described in U.S. Pat. No. 5,322,687, to tetracycline resistance using the electroporation protocol described by Mettus and Macaluso, *Appl. Environ. Microbiol.*, 56:1128–1134 (1990). Transformants were selected on Luria plates containing 10–20 ug/ml tetracycline. The resulting recombinant plasmid, designated pEG360, was isolated from the transformants, using the alkaline lysis procedure described by Maniatis et al., *Molecular Cloning: A Laboratory Manual*, Cold Spring Harbor Laboratory, Cold Spring Harbor, N.Y., (1982), and confirmed by restriction enzyme analysis. Plasmid pEG360 (FIGS. 3 and 4), containing the cryIF-IAc gene, is similar in structure to plasmid pEG337 (FIG. 5), containing the native cryIF gene, which is described in International Publication No.WO 95/02058, of Ecogen Inc.

Example 2

Construction of Recombinant Strains EG7826 and EG11724

Plasmids pEG337 and pEG360 were subsequently used to transform the B.t. host strain EG10324 subsp. *kurstaki* to tetracycline resistance using the electroporation procedure described above. Strain EG10324 is a phage-resistant variant B.t. strain EG2348, described in U.S. Pat. No. 5,188,960, and contains cryIAa, cryIAc, and cryIIA insecticidal crystal protein genes. The presence of the cryIF or cryIF-IAc gene in B.t. host strain EG10324, complementing the cryA-type genes of host strain EG10324, is designated to provide a wider spectrum of insecticidal activity against lepidopteran insects, particularly armyworms as compared with host B.t. strain EG10324. Transformants were selected on Luria plates containing 10–20 ug/ml tetracycline and confirmed by restriction enzyme analysis of their recombinant plasmids. The array of native and recombinant plasmids in the transformants were also confirmed by agarose gel electrophoresis using a modified Eckhardt agarose gel electrophoresis procedure described by Gonzalez Jr. et al., *Proc. Natl. Acad. Sci USA* 79:6951–6955 (1982). This analysis confirmed the presence of the recombinant plasmid as well as the correct array of native plasmids derived from the host strain EG10324. The resulting transformants were designated EG10324/pEG337 and EG10324/pEG360.

Plasmids pEG360 (FIG. 4) and pEG337 (FIG. 5) contain duplicate copies of a site-specific recombination site or internal resolution site (IRS) that serves as a substrate for an in vivo site-specific recombination reaction mediated by the TnpI recombinase of transposon Tn5401, described in Baum, J. A. *J. Bacteriol.* 177:4036–4042 (1995). This site-specific recombination reaction, described in U.S. Pat. No. 5,441,884, results in the deletion of non-B.t. DNA or foreign DNA elements from the crystal protein-encoding recombinant plasmids. The resulting recombinant *Bacillus thuringiensis* strains are free of foreign DNA elements, a desirable feature for genetically engineered strains destined for use as bioinsecticides for spray-on application. Strains EG10324/pEG337 and EG10324/pEG360 were modified using this in vivo site-specific recombination (SSR) system to generate two new strains, designated EG7826 and EG11724, respectively (Table 1).

TABLE 1

Recombinant B.t strains

| Strain | Alias | Recombinant plasmid | Progenitor strain |
|---|---|---|---|
| EG7826 | EG10324/pEG337Δ | pEG337Δ | EG10324/pEG337 |
| EG11724 | EG10324/pEG360Δ | pEG360Δ | EG10324/pEG360 |

Example 3

Crystal Protein Production by Strains EG7826 and EG11724

Strains EG7826 and EG11724 were inoculated into 25 ml flasks containing 8 ml of broth culture consisting of 14.4 g/l soyflour, 7.9 g/l meat peptone, 20.0 g/l cerelose, 3.1 g/l anhydrous $KH_2PO_4$, 4.7 g/l $K_2HPO_4$, 1X C2 salts (described by Donovan et al., *J. Biol Chem.* 263:561–567 (1988)), titrated to pH 7.5 with 1N NaOH.

The cultures were grown in duplicate for three days at 25° C. After three days, at which time sporulation and cell lysis had occurred, crystal protein production as quantitated by the SDS-polyacrylamide gel (PAGE) method described by Brussock, S. M., and Currier, T. C. (1990) Use of Sodium Dodecyl Sulfate-Polyacrylamide Gel Electrophoresis To Quantify *Bacillus thuringiensis* δ-Endotoxins, in Analytical Chemistry of *Bacillus thuringiensis*. (L. A.Hickle and W. L.Fitch, eds.), The American Chemical Society, pp. 78–87. The procedure was modified to eliminate the neutralization step with 3M HEPES. Crystal proteins resolved by SDS-PAGE were quantitated by densitometry using a Molecular Dynamics model 300A computing densitometer and purified CryIAc crystal protein as a standard. The results shown in Table 2 demonstrate that the CryIF-IAc strain EG1724 produced 30–40% more CryI protein than did the isogenic CryIF strain EG7826. Both strains produced comparable amounts of CryIIA protein, as expected.

TABLE 2

Crystal protein production by strain EG11724[1]

| Strain | Strain background | Recombinant plasmid, gene | CryI protein | CryIIA protein |
|---|---|---|---|---|
| EG7826 | EG10324 | pEG337Δ, cryIF | 1.0 | 1.0 |
| EG11724, culture #1 | EG10324 | pEG360Δ, cryIF-IAc | 1.33 | 1.0 |
| EG11724, culture #2 | EG10324 | pEG360Δ, cryIF-IAc | 1.39 | 1.0 |

[1]Crystal protein yield relative to the yield of strain EG7826, defined as 1.0.

Example 4

Insecticidal Activity of Purified Crystal Proteins and Recombinant Strains

The CryIF and CryIF-IAc proteins form parasporal crystals when produced in an acrystalliferous strain of *B.t.*, for instance, strain EG10368. Crystals from lysed C2 cultures, described by Donovan et al. *J. Biol. Chem.* 263:561–567 (1988), can be purified by Renografin gradient centrifugation using the procedure described by Chambers et al., *J. Bactenol.* 173:3966–3976 (1991). Crystal protein preparations, quantified using the SDS-PAGE electrophoresis described above, were used to test the insecticidal activity of CryIF and CryIF-IAc in bioassay against neonate larvae of *Spodoptera exigua*, *Trichoplusia ni*, and *Spodoptera frugiperda* and 3rd instar larvae of *Plutella xylostella*. Each bioassay consisted of eight serial dilutions in 0.005% Triton X-100. Fifty microliter aliquots were delivered to each of 32 2-ml wells containing 1 ml of an artificial agar-based diet comprising a surface area of 175 $mm^2$. The diluent alone served as a control treatment. After the diluent was allowed to dry, one larva per test species was placed in each well, for a total of 256 larvae per assay. The bioassay wells were covered and held at ~28° C. for 7 days at which time mortality was scored. Bioassay data were adjusted for control mortality using Abbott's formula (Abbott, W.S., 1925, *J. Econ. Entomol.* 18:265–267), with replication combined for composite probit analysis using the program of Daum (Daum, R. J., 1970, *Bull. Entomol. Soc. Am.* 16:10–15). The bioassay results shown in Table 3 demonstrate that CryIF and CryIF-IAc are similar with respect to their toxicity towards the insect pests tested. Mortality data was expressed as an LC50 value, in accordance with the technique of Daum, R. J., 1970, *Bull. Entomol. Soc. Am.* 16:10–15, the concentration of CryIF or CryIF-CryIAc (ng/diet well) causing 50% mortality. CryIF-IAc and CryIF exhibited comparable levels of activity against S. exigua, *S. frugiperda*, *T. ni*, and *P. xylostella*.

TABLE 3

Bioassay comparisons between purified CryIF and CryIF-IAc

| Protoxin | S. exigua | S. frugiperda | T. ni | P. xylostella |
|---|---|---|---|---|
| CryIF | 7015 (5770–8763)[2] | 691 (535–881) | 163 (105–241) | 13 (11–14) |
| CryIF-IAc | 5667 (4627–7115) | 544 (469–623) | 140 (89–203) | 21 (19–24) |

[1]pLC50 value in ng Cry protein per well.
[2]95% confidence intervals

Spore-crystal protein suspensions from spent broth cultures of strains EG7826 and EG 11724 were also used for bioassay evaluation against neonate larvae of *Spodoptera frugiperda*. Crystal proteins in the EG7826 and EG11724 broths were quantified using the SDS-PAGE electrophoresis described above. Strains EG7826 and EG 11724 are indistinguishable with respect to their toxicity towards *S. frugiperda* (Table 4).

TABLE 4

Bioassay comparison: EG7826 and EG11724 against *S. frugiperda*

| Strain | pLC50 | 95% CI |
|---|---|---|
| EG7826 | 21.8[1] | 18–26 |
| EG11724 | 23.3 | 16–33 |

[1]pLC50 value in ng CryI protein per well.

Accordingly the increased production of lepidopteran-toxic protein obtained with the chimeric CryIF-IAc protein in strain EG 11724 (Table 2) may be used to develop more concentrated bioinsecticide formulations for the control of certain lepidopteran insect pests, particularly the fall armyworm *Spodoptera frugiperda*. Increased production of lepidopteran-toxic protein also allows for more cost-effective use of the bioinsecticide product because of reduced production costs. The efficent production of spores by strain EG11724 further contributes to its toxicity towards *S. frugiperda*.

Example 5

CryI Crystal Protein Production Attributable to Chimeric CryIC-IAc Gene

A similar chimeric crystal protein gene, designated cryIC-IAc or cryIC-cryIAc, was constructed and evaluated for its ability to direct the production of a chimeric CryIC-IAc crystal protein in Bacillus thuringiensis. The chimeric CryIC-IAc protein is comprised of amino acids from about 1 to 733 of the native CryIC protein which includes the core toxin region of the CryIC protein. The remaining carboxyl terminal portion of the chimeric protein is comprised of amino acids from about 727 to 1178 of the CryIAc protein. The cryIC-IAc chimeric gene was constructed using the same strategy, described in Example 1 and illustrated in FIG. 3, for the construction of the chimeric cryIF-IAc gene, namely, the fusion of cryIC and cryIAc gene fragments at the common conserved Asp718 site found within both genes. Ligation of the cryIC and cryIAc gene fragments via the Asp718-generated cohesive ends resulted in the formation of a chimeric cryIC-IAc gene. Ligation of the Asp7188 cohesive ends regenerated codons 732 and 733 of cryIC, which are identical to codons 725 and 726 of cryIAc. The resulting gene thus comprised codons 1–733 of cryIC followed by codons 727–1178 of cryIAc.

When introduced on a recombinant plasmid into an acrystalliferous Bacillus thuringiensis host strain, such as strain EG10368 (described in U.S. Pat. No. 5,322,687), cryIC-IAc directs the production of CryIC-IAc crystal protein. A recombinant plasmid containing this gene, designated pEG928.9, is described in U.S. Pat. No. 5,441,884. Recombinant plasmids containing the native cryIC gene are described in U.S. Patent No. 5,441,884 and in International Publication No. WO 95/02058, of Ecogen Inc. Recombinant plasmids containing either the cryIC or cryIC-IAc genes were introduced into strain EG4923-4 subsp. kurstaki, a transconjugant strain containing multiple cryIAc genes and a cryIIA gene, an assessed for CryI crystal protein production in shake flask culture and in small scale fermentation. The results of those studies failed to show a >10% increase in CryI crystal protein production attributable to the chimeric cryIC-IAc gene.

The disclosures of each patent, patent application, and publication cited or described herein are hereby incorporated herein by reference in their entirety.

Various modifications of the invention in addition to those shown and described herein will be apparent to those skilled in the art from the foregoing description. Such modifications are also intended to fall within the scope of the appended claims.

REFERENCES:
U.S. Pat. No. 5,508,264
U.S. Pat. No. 5,441,884
U.S. Pat. No. 5,322,687
U.S. Pat. No. 5,188,960
U.S. Pat. No. 5,006,336
U.S. Pat. No. 4,990,332
U.S. Pat. No. 4,996,156
EPA Publication No. O 099 30
EPA Publication No. O 228 228
WO 95/30753
WO 95/30752
WO 95/02058
WO 91/16434
WO 91/07481
Abbott, W. S. (1925) J. Econ. Entomol. 18:265–267.
Aronson, A. (1993) Insecticidal toxins in Bacillus subtilis and other gram-positive bacteria. Sonensheim, A. L., Hoch, J. A., and Losick, R. (eds.). Am. Soc. Microbiol., Washington D.C., pp. 953–963.
Baum, J. A. (1995) J. Bacteriol. 177:4036–4042.
Baum et al. (1990) Appl. Environ. Microbiol. 56:3420–3428.
Benbrook et al., J Proc Bio Expo, 1986, Butterworth Stoneham, Mass. pp. 27–54.
Brussock, S. M., and Currier, T. C. (1990) Use of Sodium Dodecyl Sulfate-Polyacrylamide Gel Electrophoresis To Quantify Bacillus thuringiensis δ-Endotoxins, in Analytical Chemistry of Bacillus thuringiensis. (L. A.Hickle and W. L.Fitch, eds.), The American Chemical Society, pp. 78–87.
Capecchi, M. R. (1980) Cell, 22(2):479–488.
Chambers et al. (1991) J. Bacteriol. 173:3966–3976.
Clapp, D. W. (1993) Clin.Perinatol, 20(1):155–168.
Curiel, D. T., et al. (1991) Proc. Natl. Acad. Sci. USA, 88(19):8850–8854.
Curiel, D. T., et al. (1992) Hum. Gen. Ther., 3(2):147–154.
Daum, R. J., (1970) Bull. Entomol. Soc. Am. 16:10–15.
Donovan et al., (1988) J. Biol Chem. 263:561–567.
DuBois, N. and D. H. Dean., (1995) Biological Control 24:1741–1747.
Eglitis, M. A., and Anderson, W. F., (1988) Biotechniques, 6(7):608–614.
Eglitis, M. A., et al., (1988) Avd. Exp. Med. Biol, 241:19–27.
Fraley et al., (1983) PNAS, USA 80:4803.
Fromm, M., et al., (1985) Proc. Natl. Acad Sci. USA, 82(17):5824–5828.
Fynan, E. F., et al., (1993) Proc.Natl.Acad Sci. USA, 90(24):11478–11482.
Gonzalez Jr. et al., (1982) Proc. Natl. Acad. Sci. USA, 79:6951–6955.
Graham, F. L., and van der Eb, A. J., (1973) Virology, 54(2):536–539
Hess et al., (1968) J Adv. Enzyme Reg., 7:149.
Hofte H. and H. R. Whiteley, (1989) Microbiol. Rev. 53:242–255. Horsch et al., (1985).
Humason, Animal Tissue Techniques, W. H. Freeman and Co., 1967.
Johnston, S. A., and Tang, D. C., (1994)Methods Cell. Biol., 43(A):353–365.
Lu, L., et al., (1993) J Exp. Med. 178(6):2089–2096.
Luo et al., (1988) Plant Mol. Bio. Reporter, 6:165.
Maddock et al., (1991) Third International Congress of Plant Molecular Biology, Abstract 372.
Maniatis et al., Molecular Cloning: A Laboratory Manual, Cold Spring Harbor Laboratory, Cold Spring Harbor, N.Y., (1982).
Mettus and Macaluso, (1990) Appl. Environ. Microbiol., 56:1128–1134.
Moar, W. J., et al., (1995) Appl. Environ. Microbiol. 61:2086–2092.
Neuhaus et al., (1987) Theor. Appl. Genet., 75:30.
Omirulleh et al., (1993) Plant Molecular Biology 21:415–428.
Pena et al., (1987) Nature, 325:274.
Tang, J. D., et al., (1996) Appl. Environ. Microbiol. 62:564–569
Vasil et al., (1992) Biotechnology 10:667–674.
Wagner, E., et al., (1992) Proc.Natl.Acad.Sci. USA, 89(13):6099–6103. Weissbach and Weissbach, (1988) Methods for Plant Molecular Biology, (eds), Academic Press, Inc., San Diego, Calif.
Wong and Neumann, (1982) Biochim. Biophys. Res. Commun. 107(2):584587.
Zatloukal et al., (1992) Ann. N.Y. Acad. Sci., 660:136–153.
Zhou et al., (1983) Methods in Enzymology 101:433.

What is claimed is:

1. A microorganism comprising a CryIF core toxin-contianing portion comprising the amino acid sequence set forth in SEQ ID NO: 1 and a CryIAc tail-containing portion comprising the amino acid sequence set forth in SEQ ID NO:2.

2. The microorganism of claim 1 wherein said microorganism is *Bacillus thuringiensis*.

3. Strain EG 11724, having the NRRL accession number NRRL B-21508.

4. A chimeric protein comprising a CryIF core toxin-containing portion comprising the amino acid sequence set forth in SEQ ID NO: 1 and a CryIAc tail-containing portion comprising amino acid sequence set forth in SEQ ID NO:2.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 718 amino acids
      (B) TYPE: amino acid
      (C) STRANDEDNESS: Not Relevant
      (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:1:

```
Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
            35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300
```

-continued

```
Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
            325                 330                 335

Gly Val Phe Asn Pro Gly Gly Ala Ile Trp Ile Ala Asp Glu Asp Pro
                340                 345                 350

Arg Pro Phe Tyr Arg Thr Leu Ser Asp Pro Val Phe Val Arg Gly Gly
            355                 360                 365

Phe Gly Asn Pro His Tyr Val Leu Gly Leu Arg Gly Val Ala Phe Gln
        370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
            435                 440                 445

Thr His Arg Ser Ala Thr Pro Thr Asn Thr Ile Asp Pro Glu Arg Ile
450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
        530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
        595                 600                 605

Asp Leu Glu Arg Ala Gln Lys Ala Val Asn Ala Leu Phe Thr Ser Ile
        610                 615                 620

Asn Gln Ile Gly Ile Lys Thr Asp Val Thr Asp Tyr His Ile Asp Gln
625                 630                 635                 640

Val Ser Asn Leu Val Asp Cys Leu Ser Asp Glu Phe Cys Leu Asp Glu
                645                 650                 655

Lys Arg Glu Leu Ser Glu Lys Val Lys His Ala Lys Arg Leu Ser Asp
            660                 665                 670

Glu Arg Asn Leu Leu Gln Asp Pro Asn Phe Lys Gly Ile Asn Arg Gln
        675                 680                 685

Leu Asp Arg Gly Trp Arg Gly Ser Thr Asp Ile Thr Ile Gln Arg Gly
        690                 695                 700

Asp Asp Val Phe Lys Glu Asn Tyr Val Thr Leu Pro Gly Thr
705                 710                 715
```

(2) INFORMATION FOR SEQ ID NO:2:

(i) SEQUENCE CHARACTERISTICS:
        (A) LENGTH: 452 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:2:

```
Phe Asp Glu Cys Tyr Pro Thr Tyr Leu Tyr Gln Lys Ile Asp Glu Ser
1               5                   10                  15

Lys Leu Lys Ala Phe Thr Arg Tyr Gln Leu Arg Gly Tyr Ile Glu Asp
            20                  25                  30

Ser Gln Asp Leu Glu Ile Tyr Leu Ile Arg Tyr Asn Ala Lys His Glu
        35                  40                  45

Thr Val Asn Val Pro Gly Thr Gly Ser Leu Trp Pro Leu Ser Ala Gln
    50                  55                  60

Ser Pro Ile Gly Lys Cys Gly Glu Pro Asn Arg Cys Ala Pro His Leu
65                  70                  75                  80

Glu Trp Asn Pro Asp Leu Asp Cys Ser Cys Arg Asp Gly Glu Lys Cys
                85                  90                  95

Ala His Ser His His Phe Ser Leu Asp Ile Asp Val Gly Cys Thr
            100                 105                 110

Asp Leu Asn Glu Asp Leu Gly Val Trp Val Ile Phe Lys Ile Lys Thr
        115                 120                 125

Gln Asp Gly His Ala Arg Leu Gly Asn Leu Glu Phe Leu Glu Glu Lys
    130                 135                 140

Pro Leu Val Gly Glu Ala Leu Ala Arg Val Lys Arg Ala Glu Lys Lys
145                 150                 155                 160

Trp Arg Asp Lys Arg Glu Lys Leu Glu Trp Glu Thr Asn Ile Val Tyr
                165                 170                 175

Lys Glu Ala Lys Glu Ser Val Asp Ala Leu Phe Val Asn Ser Gln Tyr
            180                 185                 190

Asp Gln Leu Gln Ala Asp Thr Asn Ile Ala Met Ile His Ala Ala Asp
        195                 200                 205

Lys Arg Val His Ser Ile Arg Glu Ala Tyr Leu Pro Glu Leu Ser Val
    210                 215                 220

Ile Pro Gly Val Asn Ala Ala Ile Phe Glu Glu Leu Glu Gly Arg Ile
225                 230                 235                 240

Phe Thr Ala Phe Ser Leu Tyr Asp Ala Arg Asn Val Ile Lys Asn Gly
                245                 250                 255

Asp Phe Asn Asn Gly Leu Ser Cys Trp Asn Val Lys Gly His Val Asp
            260                 265                 270

Val Glu Glu Gln Asn Asn Gln Arg Ser Val Leu Val Val Pro Glu Trp
        275                 280                 285

Glu Ala Glu Val Ser Gln Glu Val Arg Val Cys Pro Gly Arg Gly Tyr
    290                 295                 300

Ile Leu Arg Val Thr Ala Tyr Lys Glu Gly Tyr Gly Glu Gly Cys Val
305                 310                 315                 320

Thr Ile His Glu Ile Glu Asn Asn Thr Asp Glu Leu Lys Phe Ser Asn
                325                 330                 335

Cys Val Glu Glu Glu Ile Tyr Pro Asn Asn Thr Val Thr Cys Asn Asp
```

```
                    340                 345                 350
Tyr Thr Val Asn Gln Glu Glu Tyr Gly Gly Ala Tyr Thr Ser Arg Asn
            355                 360                 365

Arg Gly Tyr Asn Glu Ala Pro Ser Val Pro Ala Asp Tyr Ala Ser Val
    370                 375                 380

Tyr Glu Glu Lys Ser Tyr Thr Asp Gly Arg Arg Glu Asn Pro Cys Glu
385                 390                 395                 400

Phe Asn Arg Gly Tyr Arg Asp Tyr Thr Pro Leu Pro Val Gly Tyr Val
                405                 410                 415

Thr Lys Glu Leu Glu Tyr Phe Pro Glu Thr Asp Lys Val Trp Ile Glu
            420                 425                 430

Ile Gly Glu Thr Glu Gly Thr Phe Ile Val Asp Ser Val Glu Leu Leu
            435                 440                 445

Leu Met Glu Glu
    450
```